US00PP28592P2

(12) United States Plant Patent
Probst

(10) Patent No.: US PP28,592 P2
(45) Date of Patent: Oct. 31, 2017

(54) ***COREOPSIS* PLANT NAMED 'LAUREN'**

(50) Latin Name: ***Coreopsis* hybrid**
Varietal Denomination: Lauren

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 134 days.

(21) Appl. No.: 14/756,585

(22) Filed: Sep. 21, 2015

(51) Int. Cl.
*A01H 5/02* (2006.01)

(52) U.S. Cl.
USPC ..... Plt./417

(58) Field of Classification Search
USPC ..... Plt./263.1, 417
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of hybrid *Coreopsis* named 'Lauren' characterized by its densely bushy plant habit reaching an average of 40 cm in height and 50 cm in width, its observed sterility, its floriferous and long bloom season that does not require deadheading with bloom commences in late June and lasts until frost in Kensington, Conn., its medium sized inflorescences with ray florets that are light yellow in color, its lack of requirement for vernalization to initiate flowering, its cold hardiness to at least U.S.D.A. Zone 5, and its resistance to powdery mildew and leaf spot.

2 Drawing Sheets

Botanical classification: *Coreopsis* hybrid.
Variety denomination: 'Lauren'.

CROSS REFERENCE TO A RELATED APPLICATION

This application is co-pending with a U.S. Plant Patent Application filed for a plant derived from the same breeding program that is entitled *Coreopsis* Plant Named 'Sophia' (U.S. Plant patent application Ser. No. 14,757,564).

BACKGROUND OF THE INVENTION

The present invention relates to a new and distinct cultivar of a plant botanically of hybrid origin and known as *Coreopsis*. The new cultivar will be referred to hereafter by its cultivar name 'Lauren'. 'Lauren' is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and are cold hardy at least to U.S.D.A. Zone 5 in a wide range of flower colors and plant forms on plants that do not require vernalization to initiate flowering.

The Inventor made a controlled cross in August of 2011 in his test garden in Hubbardston, Mass. between an unnamed proprietary plant from the Inventor's breeding program, reference no. G 08-8 (not patented), as the female parent and pollen that was pooled from a variety of unnamed, proprietary plants (not patented) from his breeding program as the male parent. The exact male parentage is therefore unknown. 'Lauren' was selected in September of 2012 as a single unique plant amongst the resulting seedlings.

Asexual propagation of the new cultivar was first accomplished by stem cuttings in Kensington, Conn. in September of 2012 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Lauren' as unique cultivar of *Coreopsis*.

1. 'Lauren' exhibits a compact, densely bushy plant habit reaching an average of 40 cm in height and 50 cm in width.
2. 'Lauren' has been observed to be sterile and exhibits a floriferous and long bloom season that does not require deadheading; blooming commences in late June and lasts until frost in Kensington, Conn.
3. 'Lauren' exhibits medium sized inflorescences with ray florets that are light yellow in color.
4. 'Lauren' does not require vernalization to initiate flowering.
5. 'Lauren' exhibits cold hardiness to at least U.S.D.A. Zone 5.
6. 'Lauren' exhibits resistance to powdery mildew and leaf spot.

The female parent of 'Lauren', G 08-8, differs from 'Lauren' in having inflorescences with much smaller ray florets that are fertile. 'Lauren' can also be compared to the *Coreopsis* cultivars 'Full Moon' (U.S. Plant Pat. No. 19,364), 'Galaxy' (U.S. Plant Pat. No. 21,999), and 'Sophia'. 'Full Moon' is similar to 'Lauren' in having inflorescences that are yellow in color, in being hardy to at least U.S.D.A. Zone 5 and in not requiring vernalization to initiate flowering. 'Full Moon' differs from 'Lauren' in having a larger, more open plant habit. 'Galaxy' is similar to 'Lauren' in having inflorescences with ray florets that are light yellow in color, in having a compact plant habit, in having resistance to powdery mildew, in being hardy to at least U.S.D.A. Zone 5 and in not requiring vernalization to initiate flowering. 'Galaxy' differs from 'Lauren' in having semi-double inflorescences and in having a less upright, less dense plant habit. 'Sophia' differs from 'Lauren' in having tube shaped ray florets.

BRIEF DESCRIPTION OF THE DRAWINGS

The accompanying colored photographs illustrate the overall appearance and distinct characteristics of the new *Coreopsis*. The photographs were taken of a four month-old plant of 'Lauren' as grown outdoors in a three-gallon container in Kensington, Conn.

The photograph in FIG. 1 provides a side view of a plant of 'Lauren' in bloom.

Figure 1:
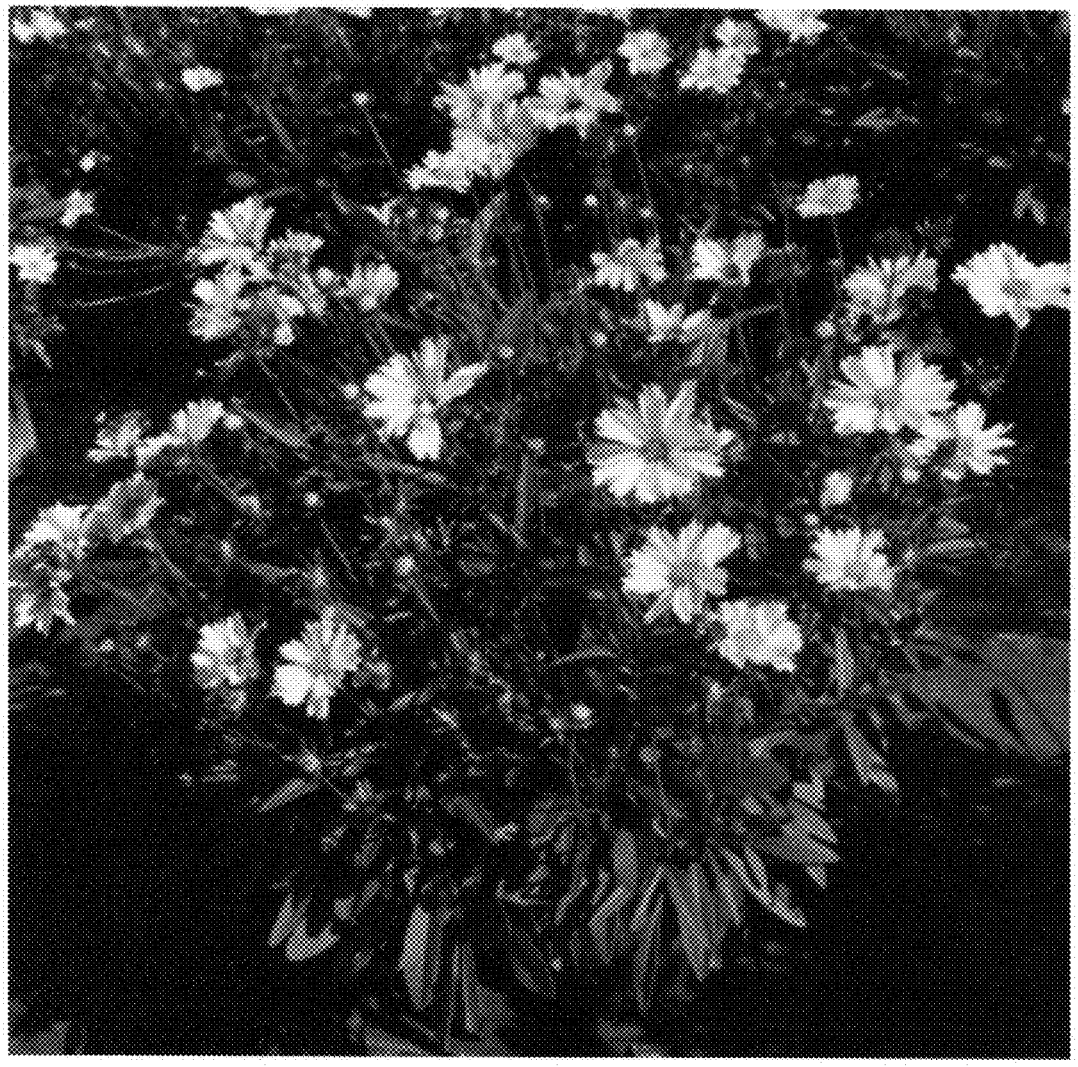
Figure 2:
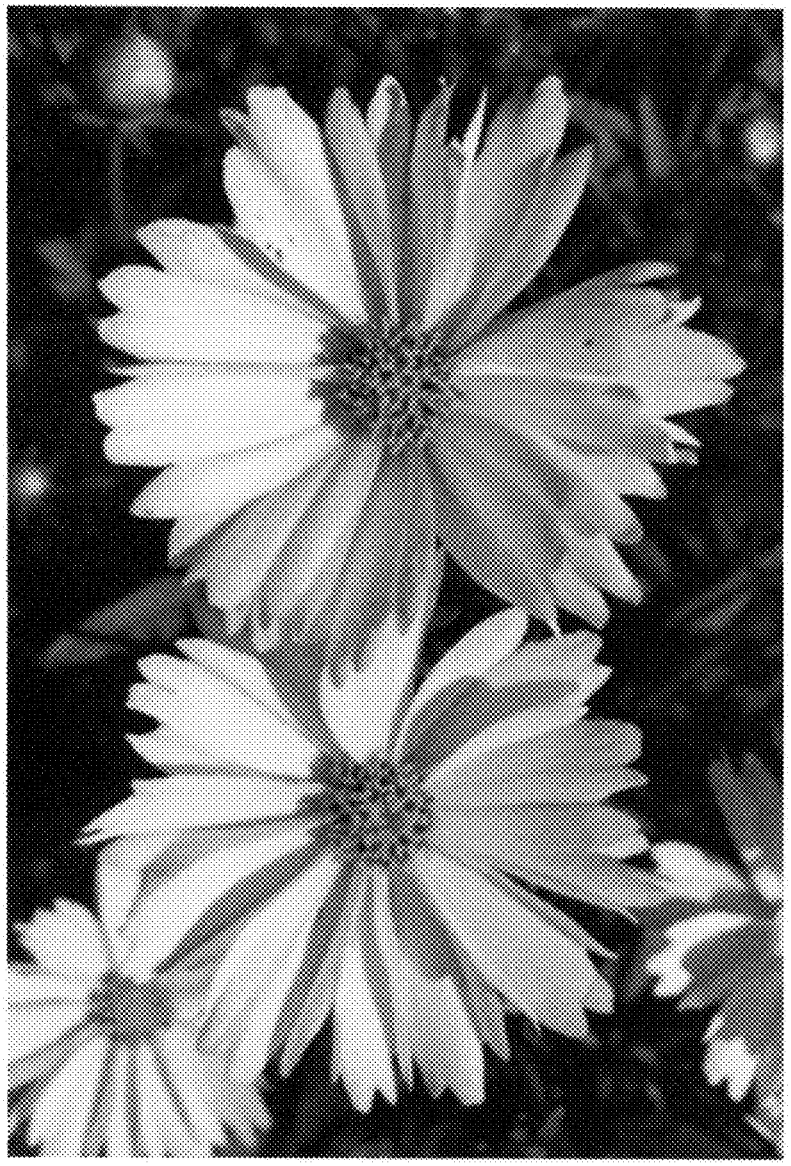

The photograph in FIG. 2 provides a close-up view of inflorescences of 'Lauren'.

The colors in the photograph may differ slightly from the color values cited in the detailed botanical description, which accurately describe the colors of the new *Coreopsis*.

DETAILED BOTANICAL DESCRIPTION

The following is a detailed description of three month-old plants of the new cultivar as grown outdoors in one-gallon containers from 128-cell plugs in Kensington, Conn. The phenotype of the new cultivar may vary with variations in environmental, climatic, and cultural conditions, as it has not been tested under all possible environmental conditions. The color determination is in accordance with The 2007 Royal Horticultural Society Colour Chart of The Royal Horticultural Society, London, England, except where general color terms of ordinary dictionary significance are used.

General description:

*Blooming period*.—Blooms from late June until frost in Kensington, Conn.

*Plant type*.—Herbaceous perennial.

*Plant habit*.—Compact and densely bushy.

*Height and spread*.—An average of 40 cm in height and 50 cm in width when grown in the landscape.

*Cold hardiness*.—At least in U.S.D.A Zone 5.

*Diseases resistance*.—Has been observed to be resistant to powdery mildew (*Podosphaera macularis*) and leaf spot (*Pseudomonas cichorii*).

*Root description*.—Fibrous when young, becoming fleshy with age, 162C in color.

*Root development*.—Roots initiate in 6 to 8 days and fully develop in a 128-cell plug in about 28 days with bottom heat and rooting hormone at optimal times of the year.

*Propagation*.—Division and stem cuttings (preferred).

*Growth rate*.—Vigorous, but stays compact.

Stem description:

*Shape*.—Oval, ridged.

*Stem color*.—Young; 138A and 138B, mature bark; N199A to N199C.

*Stem size*.—Main stems; an average of 9.5 cm in length and 5 mm in width, secondary; average of 9.5 cm in length and 2.8 mm in width.

*Stem surface*.—Slightly hirsute.

*Stem aspect*.—Upright.

*Branching habit*.—Well-branched, an average of 12 main branches, 3 secondary branches per main stem, 3 tertiary stems per secondary branches.

*Internode length*.—An average of 3 cm.

Foliage description:

*Leaf division*.—Simple.

*Leaf margins*.—Entire to trifid.

*Leaf size*.—Variable, up to 8 cm in length and 2 cm in width when entire, up to 7 cm in length and 4.1 cm in width when trifid.

*Leaf shape*.—Oblanceolate when entire, oblanceolate lobes when trifid.

*Leaf base*.—Truncate.

*Leaf apex*.—Acute.

*Leaf venation*.—Pinnate, inconspicuous, matches leaf color on upper and lower surface.

*Leaf attachment*.—Sessile.

*Leaf arrangement*.—Opposite.

*Leaf number*.—An average of 10 per stem (5 pairs).

*Leaf surface*.—Upper surface slightly hirsute and dull, lower surface very slightly hirsute and dull.

*Leaf color*.—Young and mature upper surface; 138A, young and mature lower surface; 138A to 138B.

Inflorescence description:

*Inflorescence type*.—Composite with a single row of overlapping ray florets surrounding disk florets in the center.

*Lastingness of inflorescence*.—8 to 10 days until senescence of ray flowers, longer in cool temperatures, bracts and disk flowers are persistent.

*Fragrance*.—None detected.

*Quantity of inflorescences*.—An average of 10 per main branch.

*Inflorescence size*.—An average of 6 mm in depth and up to 5.5 cm in diameter.

*Inflorescence buds*.—Average of 6 cm in depth and in diameter, spherical in shape with a flattened top, color; a blend of 144C and 183D.

*Peduncle*.—Average of 8.5 cm in length and 1.2 mm in width, glabrous surface, 138A in color, strong.

Involucral bracts:

*Bract number*.—8.

*Bract arrangement*.—Bracts surround receptacle in a campanulate form, held close to lower surface of ray florets.

*Bract size*.—An average of 9 mm in length and 4.5 mm in width.

*Bract color*.—Translucent; upper portion, a blend between 151A and 175A, base 144A to 144B.

*Bract texture*.—Outer and inner surface; glabrous and satiny.

*Bract apex*.—Acute.

*Bract base*.—Truncate.

*Bract margins*.—Entire.

*Bract shape*.—Ovate.

Ray florets (sterile):

*Number*.—An average of 9 arranged primarily in one row.

*Shape*.—Oblong to obovate.

*Size*.—An average of 2.5 cm in length and 1.2 cm in width.

*Apex*.—3 notched.

*Base*.—Cuneate.

*Margins*.—Entire with apex notched.

*Aspect*.—Held outward, slightly recurved.

*Texture*.—Glabrous on upper and lower surface.

*Color*.—When opening inner surface; 7A, opening outer surface; 5A, when fully open upper surface; 7A, fully open lower surface; 6B.

Disk flowers (perfect):

*Shape*.—Tubular, corolla is fused, flared at apex.

*Number*.—About 80.

*Size*.—About 3 mm in length and 0.5 mm in width.

*Color*.—En masse; a blend of 166A and 12B, corolla tube; 177B in color.

*Receptacle*.—About 6 mm in diameter and 2 mm in depth, color; 10C to 10D.

Reproductive organs:

*Presence*.—Disk flowers are perfect, ray flowers are sterile.

*Gynoecium*.—1 Pistil, 4 mm in length, style is very fine, translucent and 177B in color, star-shaped stigma is a blend of 166A to 12B in color, ovary is 1 mm in length, 0.5 mm in width, inferior, and 150D in color.

*Androcoecium*.—3 stamens, fused into tube surrounding style, 1 mm in length and 0.2 mm in width, about 166A in color, pollen is moderate in quantity and 14A in color.

*Fruit/seed*.—Presumed to be sterile, no seed has been observed to date.

It is claimed:

1. A new and distinct cultivar of *Coreopsis* plant named 'Lauren' as herein illustrated and described.

* * * * *